(12) United States Patent
Tsuyuki

(10) Patent No.: US 6,985,170 B1
(45) Date of Patent: Jan. 10, 2006

(54) IMAGE PICKUP APPARATUS

(75) Inventor: Hiroshi Tsuyuki, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/430,074

(22) Filed: Oct. 29, 1999

(30) Foreign Application Priority Data

Oct. 29, 1998 (JP) ................................ 10-322955

(51) Int. Cl.
*H04N 13/00* (2006.01)
*A61B 1/06* (2006.01)

(52) U.S. Cl. .......................................... 348/65; 348/42

(58) Field of Classification Search ................. 348/42, 348/43–47, 62–92; 600/101, 102, 103, 160, 600/104, 109–112, 129, 167, 168, 170–182; 359/368, 385, 389; 362/293, 574; 358/98; 606/10; A61B 1/06; H04N 13/00, 7/00
See application file for complete search history.

(56) References Cited

U.S. PATENT DOCUMENTS

| | | | |
|---|---|---|---|
| 4,816,909 A | * | 3/1989 | Kimura et al. ................. 348/71 |
| 4,916,534 A | * | 4/1990 | Takhashi et al. ............... 358/98 |
| 4,977,450 A | * | 12/1990 | Yokota .......................... 348/71 |
| 5,177,605 A | | 1/1993 | Takahashi et al. ............. 348/65 |
| 5,514,127 A | * | 5/1996 | Shanks .......................... 606/10 |
| 5,997,472 A | * | 12/1999 | Bonnell et al. ............. 600/109 |
| 6,028,622 A | * | 2/2000 | Suzuki .......................... 348/65 |
| 6,099,146 A | * | 8/2000 | Imamura et al. ............. 362/293 |
| 6,124,883 A | * | 9/2000 | Suzuki et al. .................. 348/68 |
| 6,148,227 A | * | 11/2000 | Wagnieres et al. .......... 600/476 |
| 6,293,911 B1 | * | 9/2001 | Imaizumi et al. ............ 600/160 |
| 6,537,211 B1 | * | 3/2003 | Wang et al. ................. 600/178 |

FOREIGN PATENT DOCUMENTS

JP          1-12547          8/1989

* cited by examiner

*Primary Examiner*—Tung Vo
(74) *Attorney, Agent, or Firm*—Pillsbury Winthrop Shaw Pittman LLP

(57) ABSTRACT

An image pickup apparatus comprising an optical element which absorbs rays having specific wavelengths, an optical element which reflects rays having specific wavelengths and an organic color mosaic filter, wherein a total spectral characteristic of the optical elements satisfies the following condition:

$0.45 \leq |\Delta T/\Delta W| \leq 0.75$.

14 Claims, 11 Drawing Sheets

IMAGE PICKUP APPARATUS

BACKGROUND OF THE INVENTION a) Field of the Invention

The present invention relates to an image pickup apparatus, and more specifically an image pickup apparatus which uses a composite filter.

b) Description of the Prior Art

It is general to use an infrared cut filter in combination with a single plate color CCD in order to cut detrimental near infrared rays.

Known as infrared cut filters are an absorption type filter which absorbs rays having specific wavelengths dependently on concentrations of pigments and a reflection type filter using an interference film which cancels only rays having specific wavelengths by utilizing a phase difference.

Out of these infrared cut filters, the absorption type infrared cut filter must have a certain definite thickness to obtain a specific spectral characteristic dependently on the concentrations of the pigment. Accordingly, the absorption type infrared cut filter is not always optimum for an image pickup apparatus which is restricted in a longitudinal direction, an endoscope or the like in particular. Furthermore, the absorption type infrared cut filter has a cutoff characteristic which traces a gentle curve and is not preferable from a viewpoint of a color reproducibility.

On the other hand, the reflection type filter is less restricted in the longitudinal direction and has a steep cutoff characteristic, thereby having a relatively high color reproducibility. However, the reflection type filter has a highly reflective coated surface, and may produce flare and ghost.

A composite filter is known as a filter which utilizes merits and makes up for defects of the filters. Japanese Utility Model Kokai Publication No. Hei 1-125417 (U.S. Pat. No. 5,177,605) discloses an example of composite filter shown in FIGS. 1A and 1B which is composed of a combination of an absorption type filter and a reflection type filter to enhance a color reproducibility and reduce ghost. In FIG. 1A, a reference symbol F(A) represents the absorption type filter and a reference symbol F(R) designates the reflection type filter, and in FIG. 1B, a reference symbol T[F(A)] denotes spectral transmittance of the absorption type filter, a reference symbol T[F(R)] represents spectral transmittance of the reflection type filter, a reference symbol T[f(A)F(R)] designates total spectral transmittance, a reference symbol T denotes transmittance and a reference symbol W represents a wavelength.

This filter mentioned as a conventional example lowers an intensity of ghost rays which are produced by multiple reflections between the reflection type filter and another highly reflective surface with the absorption type filter, and corrects a cutoff characteristic of the absorption type filter with a steep cutoff characteristic of the reflection type filter.

However, it is actually impossible to obtain a function which is effective to satisfy a requirement described above simply by combining different kinds of filters as in the conventional example. Furthermore, the utility model mentioned above makes no disclosure of a concrete filter which is effective to satisfy the requirement described above nor a characteristic of the filter.

Though the utility model which discloses the conventional example describes problems of color reproducibility, ghost and the like which are attributed to the filters themselves, it makes no reference to a characteristic of a CCD used in combination with the composite filter. Optimization of an infrared filter is largely different dependently on a characteristic of a CCD used in combination therewith, that of a color mosaic filter in particular.

A single plate color filter generally prepares color difference signals with four vertical lines as shown in FIG. 2, and each line of a mosaic filter is composed by combining yellow Ye, cyanic Cy, magenta Mg and green G as listed below:

First line: Ye, Cy, Ye, Cy
Second line: Mg, G, Mg, G
Third line: Ye, Cy, Ye, Cy
Fourth line: G, Mg, G, Mg An n-th color difference signals (R–Y, B–Y) in an A field are prepared by Cy and Ye on the first line, and G and Mg on the second line, whereby R–Y=2R–G.

Furthermore, an (n+1)th color difference signals in the A field are prepared by Cy and Ye on the third line, and G and Mg on the fourth line, whereby B–Y=2B–G.

The reference symbol R represents a red signal, the reference symbol G designates green signal, the reference symbol B denotes a blue signal and the reference symbol Y represents a luminance signal.

When an intense light is incident on a CCD to set it in a saturated condition, signal levels of the color signals R, G and B are set at 1:1:1. However, output signals are not always set at 1:1:1 since a spectral characteristic of the CCD itself has a peak in an infrared region. That is, only a signal from the nth line in the S field including the color signal R is set at a high level. As a result, noise appears on a monitor as red light and shade.

An infrared cut filter is usually used to adjust a level of the red signal thereby preventing such noise to be produced.

In case of an instrument such as a medical endoscope which is used to observe an interior of a human body in particular, an organ to be observed is mainly reddish. Accordingly, the horizontal stripe noise is liable to be noticeable. Furthermore, such an endoscope uses a light source which emits a light containing infrared spectral components in amounts relatively larger than those in natural light and fluorescent light, thereby inevitably requiring an infrared cut filter.

Though it is possible to cancel or reduce such noise by multiplying an output signal by a certain coefficient, needless to say, it is inevitably necessary for this purpose to use an exclusive circuit and customize a CCD. A manufacturing cost of an image pickup apparatus is enhanced in this case.

In a field of medical treatments, many imaging systems for public use have recently been adopting DSPs (digital signal processors) which have high performance and are manufactured at low costs. The DSPs themselves are frequently adopted for appliances which process large amounts of information such as compressed voice and compressed images to exhibit their effects for accelerating processing speeds. In these cases, signals from the CCDs are processed dependently on specifications for the DSPs.

In case of an endoscope system which handles a plurality of endoscopes using different CCDs, it is naturally difficult to customize signal processing circuits which are specialized for individual fields or individual instruments. Accordingly, it is obliged to rely on infrared cut filters as means to reduce noise such as that described above.

The description of the characteristics of the CCDs is not provided in Japanese Utility Model Kokai Publication No. Hei 1-125417 (U.S. Pat. No. 5,177,605).

In an endoscope system which controls a plurality of endoscopes with a single CCU (camera control unit), specifications for optimum endoscopes are different dependently on fields of products of optical instruments. The inexpensive absorption type infrared cut filter is mainly used, for example, in a medical endoscope for digestive systems or external TV sets for which a relatively loose restriction is imposed on a size of an endoscope. In contrast, the reflection type infrared cut filter which is advantageous for compact configuration is used in an endoscope for bronchi for which a relatively severe restriction is imposed on the size of the endoscope. Furthermore, a CC to be used in an endoscope is selected so as to be optimum for a field of use.

Different kinds of filters and different kinds of CCDs are selected for the endoscope which are used in the endoscope system as described above. Accordingly, a color reproducibility of the endoscope system is different dependently on endoscope used in the endoscope system and it may be difficult to correct this difference with the CCU.

SUMMARY OF THE INVENTION

A primary object of the present invention is to provide a composite infrared cut filter which has a high color reproducibility, produces little ghost and is capable of reducing noise as well as an image pickup apparatus which uses the filter.

Another object of the present invention is to provide an endoscope system which handles a plurality of different kinds of endoscopes and is configured to be capable of obtaining images from the endoscopes with nearly the same color reproducibility.

The image pickup apparatus according to the present invention is characterized in that it comprises an optical element which absorbs rays having specific wavelengths, an optical element which reflects rays having specific wavelengths, an organic color mosaic filter and an image pickup device, and that a total spectral characteristic of a combination of the optical elements mentioned above satisfies the following condition (1):

$$0.45 \leq |\Delta T/\Delta W| \leq 0.75 \qquad (1)$$

wherein the reference symbol $\Delta T$ represents a difference between transmittance T(600) at a wavelength of 600 nm and transmittance T (550) at a wavelength of 550 nm, or $\Delta T(\%) = T(600) - T(550)$, and the reference symbol $\Delta W$ designates 50 nm.

If $|\Delta T/\Delta W|$ is represented by A in the condition (1) and A has a value exceeding the lower limit of 0.45, the rays having wavelengths within a region where the horizontal stripe noise may not be cut off sufficiently, thereby producing unallowable noise. If A has a value exceeding the upper limit of 0.75, in contrast, the noise will be scarcely noticeable but visible rays will be remarkably cut off, thereby making it impossible to obtain a preferable color reproducibility.

An endoscope system often controls a plurality of endoscopes with a single camera control unit (CCU) as described above. This is because optimum specifications for endoscopes are different dependently on fields of optical instruments, whereby the endoscopes use different filters, different DDCs and have different color reproducibilities.

It is desirable to optimalize a spectral characteristic of a composite filter to each endoscope so that different endoscopes in such an endoscope system finally have color reproducibilities which are substantially the same.

The composite filter according to the present invention is composed by combining a reflection type filter and a transmission type filter which have different spectral characteristics, and has a spectral characteristic which can be modified relatively easily. Though it is conceivable to use only an absorption type filter and modify a spectral characteristic by changing its thickness, a spectral characteristic may be modified by changing a film configuration of a reflection type filter.

Another endoscope system according to the present invention comprises a camera control unit (CCU) to which a plurality of different kinds of endoscopes (having different specifications) are to be connected, a light source unit for illuminating an object and a TV monitor which displays an image of the object: the plurality of endoscopes of the endoscope system according to the present invention comprising image pickup devices having spectral characteristics different from one another and an optical element which absorbs or reflects rays having specific wavelengths to obtain a predetermined spectral characteristic.

When color reproducibilities cannot be equalized even with the composite filter or when a sufficiently high color reproducibility is not obtained since it is not preferable to use a plurality of different filters, it is possible to configure the endoscope system so that it selectively uses a plurality of color matrix circuits optimum for respective products which are preliminarily prepared on a side of the CCU. For example, it is possible to configure the endoscope system so that an electric resistor is selectively connected in a CCU connector for each endoscope, and the CCU detects a signal from the electric resistor and selects a color matrix. Alternately, it is possible to configure the endoscope system to be capable of selecting color matrix circuits which are customized by a user for individual ways of use.

DETAILED DESCRIPTION OF THE PREFERRED EMBODIMENTS

Figure 3:
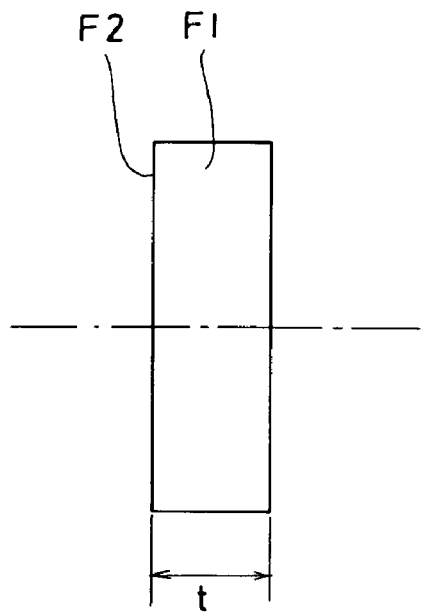
FIG. 3 is a sectional view illustrating a composition of a composite filter to be used in a first embodiment of the present invention.
Figure 5:
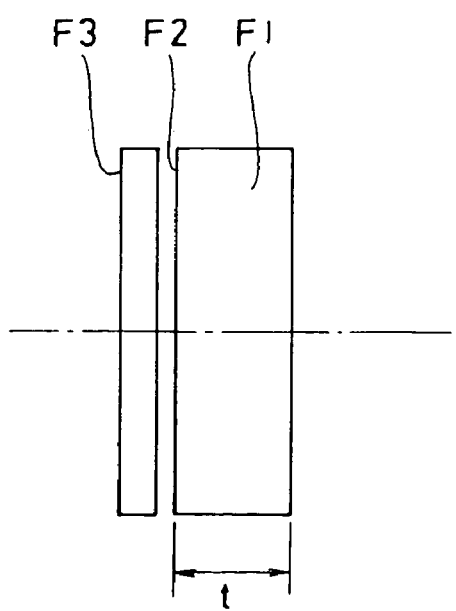
FIG. 5 is a sectional view illustrating a composition of a composite filter to be used in a second embodiment of the present invention.
Figure 4:
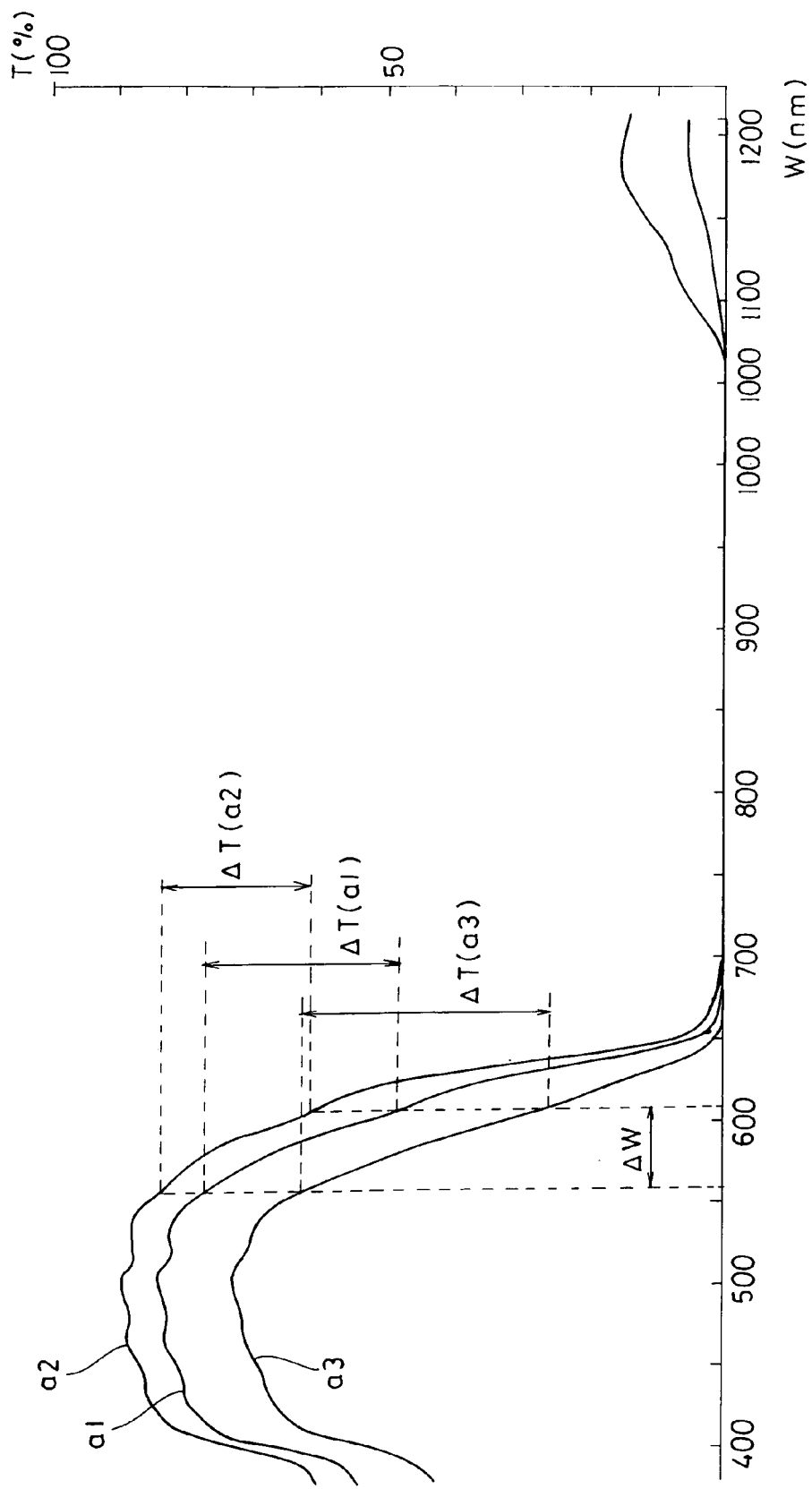
FIG. 4 is a diagram illustrating a spectral characteristic of the filter shown in FIG. 3.

The image pickup system according to the present invention comprises a composite filter described below and a first embodiment of the present invention is characterized by a composition of the composite filter. The composite filter is composed as shown in FIG. 3, wherein a reference symbol F1 represents an absorption type infrared cut filter and a reference symbol F2 designates a reflectin type cut coat formed on a surface of the absorption type infrared cut filter F1. The composite filter is composed by combining two kinds of filters as described above. FIG. 4 shows a total spectral transmittance characteristic of these filters combined with each other.

Examinations provided a result that a color reproducibility was enhanced but the noise like the horizontal stripes could not be suppressed to an unnoticeable level when only reflection type infrared cut filters were used. Furthermore, the reflection type infrared cut filters produced ghost peculiar thereto. The reflection type filters used for the examinations had a characteristic to exhibit half a value of transmittance at wavelengths of approximately from 630 to 650 nm and a transmittance of approximately 0% at about 710 nm. That is, the examinations indicated that the noise can be reduced by cutting off near infrared rays which have wavelengths shorter than approximately 630 nm and a color reproducibility can be enhanced by imparting a steep cutoff characteristic which cuts off near infrared rays in the vicinity of approximately 700 nm as far as possible.

However, it is undesirable to use the reflection type filters which have the steep characteristic since they cut off visible rays when their cutoff regions are shifted toward a shorter wavelength side.

Used as an image pickup device for the examinations described above was a single plate color CCD which comprised an organic complementary color mosaic filter.

Furthermore, the examinations indicated that a combination only of absorption type infrared cut filters could reduce the horizontal stripe noise and ghost, but provided a color reproducibility lower than that available with the combination only of the reflection type filters. The filters used for the examinations exhibited half a value in the vicinity of approximately 610 nm.

The composite filter preferred as a first embodiment of the present invention is composed by combining the absorption type filter F1 and the reflection type filter F2 described above as shown in FIG. 3, and has any one of total spectral characteristics a1, a2 and a3 shown in FIG. 4. In other words, the composite filter preferred as the first embodiment consists of a first optical element F1 which is the absorption type filter and a second optical element F2 which is the reflection type filter, and has the total spectral characteristic shown in FIG. 4.

Out of composite filters which have the total spectral characteristics a1, a2 and a3, one having the characteristic a1 in particular reduces ghost and noise without fail, and provides a most desirable color reproducibility. However, manufacturing errors of the filter and variations of the spectral characteristic dependent on an angle of incidence on a coating must be taken into consideration. It is therefore desirable that the composite filter has a spectral characteristic which exhibits transmittance not lower than 40% at a wavelength of 600 nm and transmittance not higher than 5% at a wavelength of 700 nm, and has a value of A which is within a range of A=0.6±0.1.

This is because a characteristic at wavelengths from 600 to 700 nm influences on reduction of ghost and noise as well as a color reproducibility.

Furthermore, the composite filters which have the characteristics a2 and a3 permits changing thicknesses t thereof within ranges where the noise and ghost can be reduced while maintaining color reproducibilities at practical levels, characteristics a2 and a3 allows a thickness t of a filter.

That is, a filter may be thinned or thickened dependently on purposes of use in a field of products of optical instruments or a field of endoscopes in particular. However, a practically usable composite filter can be composed without degrading a color reproducibility within a range where the above-mentioned condition is satisfied.

The filter preferred as the first embodiment of the present invention has a value of A which is listed below;

(Filter having characteristic a1)

$A=|\Delta T(a1)/\Delta W|=|(46.72-76.36)/50|\approx 0.59$ (Filter having characteristic a2)

$A=|\Delta T(a2)/\Delta W|=|(61.06-83.54)/50|\approx 0.45$ (Filter having characteristic a3)

$A=|\Delta T(a3)/\Delta W|=|(25.01-61.93)/50|\approx 0.74$

Furthermore, the composite filter preferred as the first embodiment has a thickness which is listed below:

(Filter having characteristic a1)

$t=1.6$ mm (Filter having characteristic a2)

$t=1$ mm (Filter having characteristic a3)

$t=3$ mm

The thickness t does not strictly define a thickness of the composite filter and a filter is sufficiently usable so far as it satisfies the condition.

When the composite filter according to the present invention is to be used in an endoscope, it is desirable to configure it not only to reduce ghost and noise and enhance a color reproducibility but also to allow the endoscope to be configured compact. It is therefore conceivable to configure the absorption type filter to be thin. When the absorption type filter is configured extremely thin as described above, however, it cannot expect that the composite filter exhibits an effect to reduce ghost and noise.

In a certain field of application, however, a demand for compact configuration of an endoscope is so strong and must be preferential.

Examinations indicated that ghost and noise are not noticeable when A has a value within a range defined by the following condition (1—1):

$$0.35 \leq A \leq 0.75 \tag{1—1}$$

In other words, it is desirable that $0.35 \leq |\Delta T/\Delta W| \leq 0.75$.

When the above-mentioned condition (1—1) is satisfied, ghost and noise are optically aggravated as compared with those allowed by the composite filter preferred as the first embodiment described above, but a color reproducibility can be enhanced by color correction with the camera control unit CCU, thereby enhancing an image quality as a result.

A complementary color mosaic filter has fine filters of Cy, Mg, Ye and G which are arranged in mosaic as described above and problematic noise is largely dependent on a spectral characteristic of Mg. This is because a photodiode has a sensitivity which is relatively high in the near infrared region.

The composite filter according to the present invention exhibits a noise reducing effect when it is combined a CCU which has a spectral characteristic of Mg exhibiting transmittance not lower than 50% at 600 nm.

Though the first embodiment of the present invention is advantageous from a viewpoint of brightness as already described with reference to the CCD comprising the complementary color mosaic filter, the composite filter may be combined with a CCD using a primary color filter which is excellent in a color reproducibility when brightness is not restricted so strictly.

Furthermore, the composite filter preferred as the first embodiment of the present invention is capable of cutting rays within a wavelength region of a semiconductor laser beam.

While laser scalpels have conventionally been often used for treatments with endoscope, semiconductor laser has recently been used as a laser light source. This is because semiconductor laser apparatuses provide merits of compactness and low cost.

However, rays having wavelengths of approximately 700 nm to 830 nm within a wavelength region of the semiconductor laser are unnecessary to form a favorable image and detrimental for the CCD. This is because the CCD itself has a sensitivity covering the wavelength region of the semiconductor laser, thereby skipping white on an image of an object.

Though a semiconductor laser cut filter is used to cut off the rays having the wavelengths within the wavelength region of the semiconductor laser in such a case, it is not preferable to use such a filter since it increases a number of filters used.

The composite filter preferred as the first embodiment is configured to cut off rays having wavelengths of approximately 700 to 830 nm within the wavelength region of the semiconductor laser and exhibits spectral transmittance of approximately 0% in this wavelength region.

The composite filter preferred as the first embodiment of the present invention is capable of cutting off laser rays without using another filter even when a semiconductor laser is used. That is, the composite filter is capable of cutting the laser rays simultaneously with the infrared rays, and eliminates the necessity to use a semiconductor laser ray cut filter, thereby making it possible to configure an image pickup system more compact and manufacture it at a lower cost.

Figure 1A:
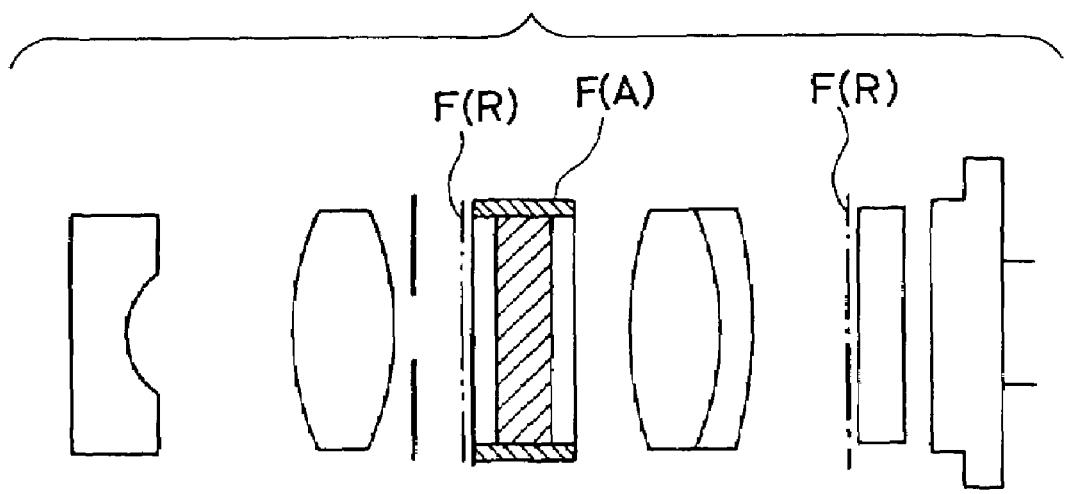
FIG. 1A is a sectional view illustrating a composition of a conventional image pickup optical system.
Figure 1B:
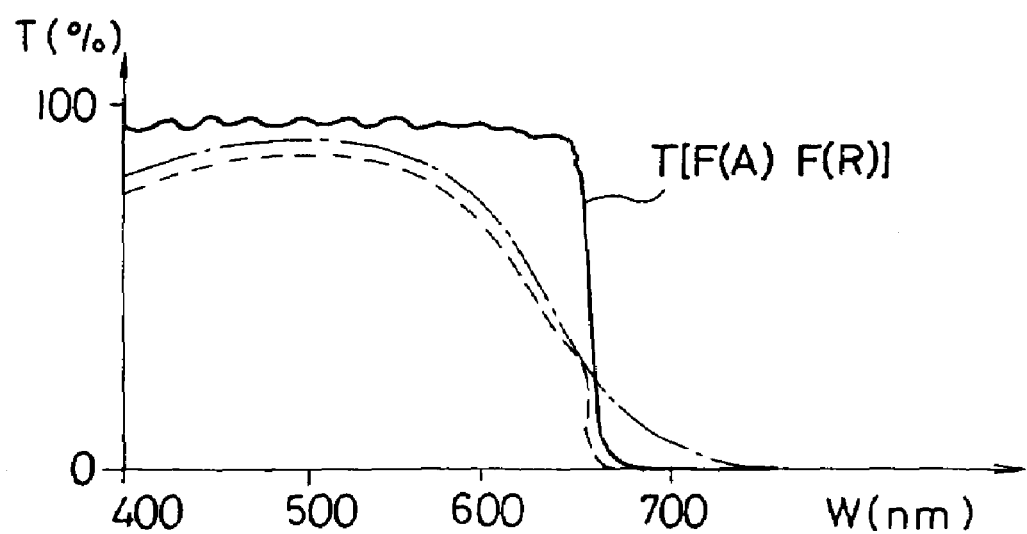
FIG. 1B is a diagram illustrating spectral transmittance of a composite filter used in the image pickup optical system mentioned above.
Figure 2:
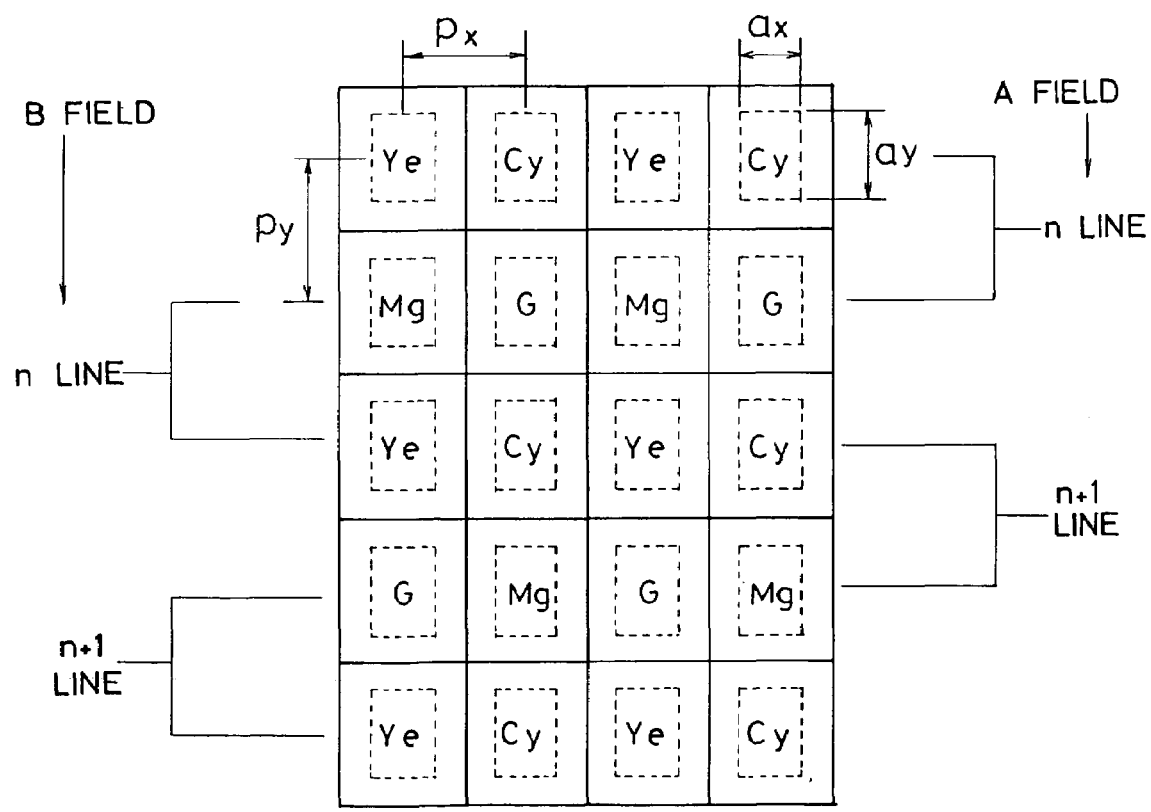
FIG. 2 is a diagram showing an example of arrangement of color separation filters.

A second embodiment of the composite filter to be used in the image pickup system according to the present invention has a composition shown in FIG. 2, wherein a reference symbol F1 represents an absorption type filter, and reference symbols F2 and F3 designate reflection type filters. The second embodiment has the composition wherein the reflection type filter F3 is added to the filter preferred as the first embodiment shown in FIG. 3. That is, the composite filter preferred as the second embodiment consists of a first optical element F1 which is the absorption type filter, and second and third optical elements F2 and F3 which are the reflection type filters.

The second embodiment is a filter having a configuration which is suited for use not with a semiconductor laser but also a YAG laser.

Figure 6:
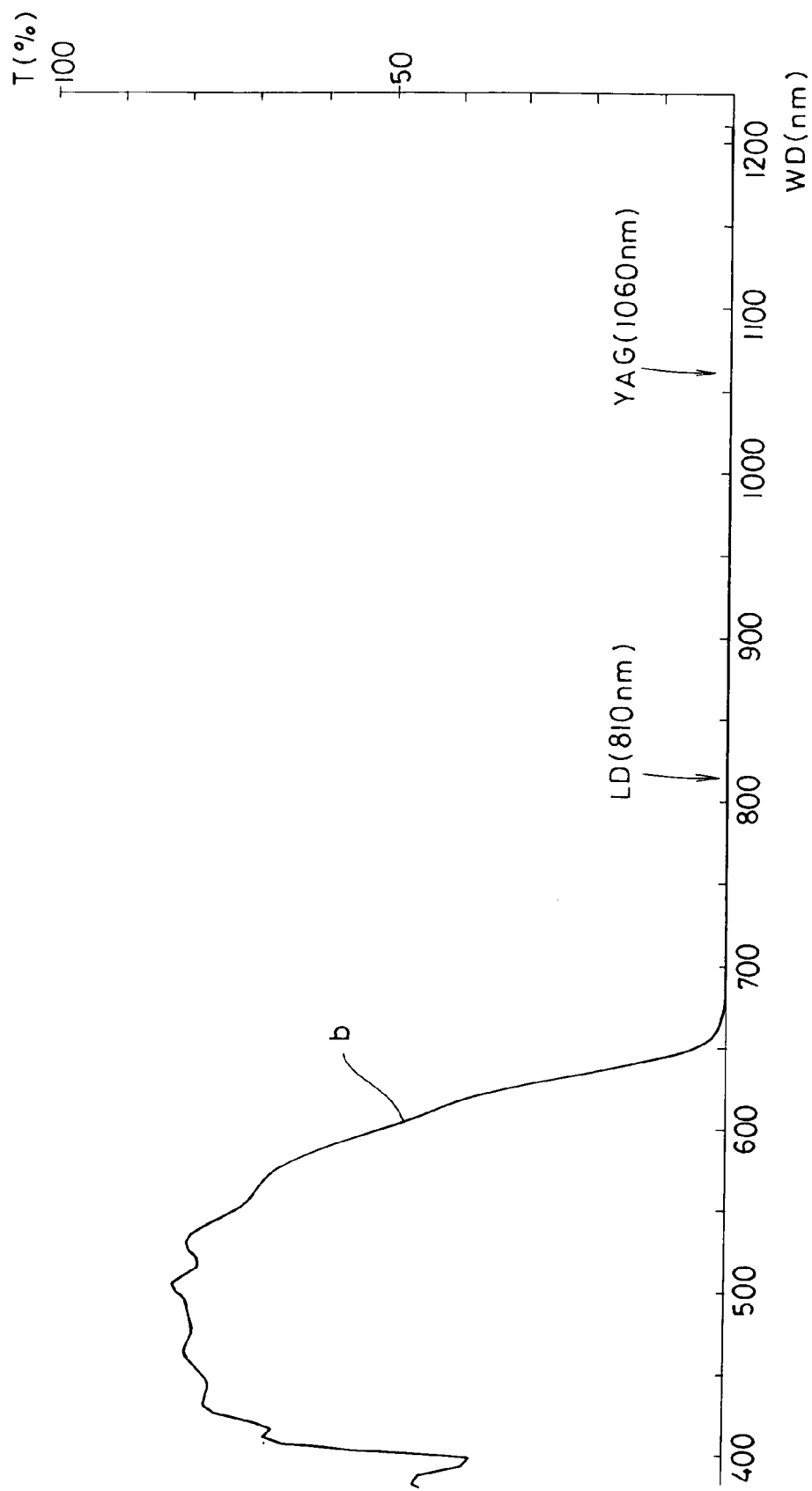
FIG. 6 is a diagram illustrating a spectral characteristic of the composite filter shown in FIG. 5.

The YAG laser has a wavelength region of approximately 1060 nm which cannot be cut off sufficiently with the composite filter preferred as the first embodiment. The second embodiment which comprises the additional reflection type filter F3 has a spectral characteristic illustrated in FIG. 6. As apparent from this drawing, the composite filter preferred as the second embodiment has transmittance of approximately 0 not only in the wavelength region of the semiconductor laser but also in the wavelength region of the YAG laser which is approximately 1060 nm. Taking into manufacturing of the filter into consideration, it is desirable to configure the YAG filter so as to have a cutoff frequency on the order of 1060±20 nm.

The following table lists transmittance of the filters shown in FIGS. 4 at various wavelengths:

| Wavelength(nm) | Transmittance T (%) | | | |
|---|---|---|---|---|
| | a1 | a2 | a3 | b |
| 380 | 0.557 | 0.608 | 0.456 | 0.456 |
| 390 | 0.622 | 0.672 | 0.518 | 0.379 |
| 400 | 0.730 | 0.786 | 0.615 | 0.653 |
| 410 | 0.763 | 0.819 | 0.647 | 0.669 |
| 420 | 0.788 | 0.844 | 0.673 | 0.753 |
| 430 | 0.794 | 0.849 | 0.680 | 0.766 |
| 440 | 0.800 | 0.852 | 0.689 | 0.765 |
| 450 | 0.814 | 0.866 | 0.703 | 0.787 |
| 460 | 0.824 | 0.877 | 0.714 | 0.800 |
| 470 | 0.819 | 0.871 | 0.711 | 0.787 |
| 480 | 0.824 | 0.875 | 0.716 | 0.794 |
| 490 | 0.830 | 0.881 | 0.723 | 0.800 |
| 500 | 0.836 | 0.886 | 0.729 | 0.820 |
| 510 | 0.814 | 0.866 | 0.705 | 0.779 |
| 520 | 0.815 | 0.869 | 0.701 | 0.794 |
| 530 | 0.813 | 0.871 | 0.691 | 0.790 |
| 540 | 0.799 | 0.863 | 0.668 | 0.746 |
| 550 | 0.764 | 0.835 | 0.619 | 0.704 |
| 560 | 0.723 | 0.807 | 0.560 | 0.690 |
| 570 | 0.680 | 0.779 | 0.495 | 0.663 |
| 580 | 0.624 | 0.739 | 0.419 | 0.612 |
| 590 | 0.544 | 0.674 | 0.330 | 0.538 |
| 600 | 0.467 | 0.611 | 0.250 | 0.461 |
| 610 | 0.401 | 0.560 | 0.184 | 0.398 |
| 620 | 0.286 | 0.432 | 0.109 | 0.283 |
| 630 | 0.152 | 0.252 | 0.047 | 0.152 |
| 640 | 0.045 | 0.082 | 0.011 | 0.045 |
| 650 | 0.013 | 0.027 | 0.003 | 0.013 |
| 660 | 0.006 | 0.014 | 0.001 | 0.006 |
| 670 | 0.003 | 0.008 | 0.000 | 0.003 |
| 680 | 0.001 | 0.003 | 0.000 | 0.001 |
| 690 | 0.000 | 0.001 | 0.000 | 0.000 |
| 700 | 0.000 | 0.001 | 0.000 | 0.000 |
| 710 | 0.000 | 0.001 | 0.000 | 0.000 |
| 720 | 0.000 | 0.001 | 0.000 | 0.000 |
| 730 | 0.000 | 0.000 | 0.000 | 0.000 |
| 740 | 0.000 | 0.000 | 0.000 | 0.000 |
| 750 | 0.000 | 0.000 | 0.000 | 0.000 |
| 760 | 0.000 | 0.000 | 0.000 | 0.000 |
| 770 | 0.000 | 0.000 | 0.000 | 0.000 |
| 780 | 0.000 | 0.000 | 0.000 | 0.000 |
| 790 | 0.000 | 0.000 | 0.000 | 0.000 |

-continued

| Wavelength(nm) | Transmittance T (%) | | | |
|---|---|---|---|---|
| | a1 | a2 | a3 | b |
| 800 | 0.000 | 0.000 | 0.000 | 0.000 |
| 810 | 0.000 | 0.000 | 0.000 | 0.000 |
| 820 | 0.000 | 0.000 | 0.000 | 0.000 |
| 830 | 0.000 | 0.000 | 0.000 | 0.000 |
| 840 | 0.000 | 0.000 | 0.000 | 0.000 |
| 850 | 0.000 | 0.000 | 0.000 | 0.000 |
| 860 | 0.000 | 0.000 | 0.000 | 0.000 |
| 870 | 0.000 | 0.000 | 0.000 | 0.000 |
| 880 | 0.000 | 0.000 | 0.000 | 0.000 |
| 890 | 0.000 | 0.000 | 0.000 | 0.000 |
| 900 | 0.000 | 0.000 | 0.000 | 0.000 |
| 910 | 0.000 | 0.000 | 0.000 | 0.000 |
| 920 | 0.000 | 0.000 | 0.000 | 0.000 |
| 930 | 0.000 | 0.000 | 0.000 | 0.000 |
| 940 | 0.000 | 0.000 | 0.000 | 0.000 |
| 950 | 0.000 | 0.000 | 0.000 | 0.000 |
| 960 | 0.000 | 0.000 | 0.000 | 0.000 |
| 970 | 0.000 | 0.001 | 0.000 | 0.000 |
| 980 | 0.000 | 0.001 | 0.000 | 0.000 |
| 990 | 0.000 | 0.001 | 0.000 | 0.000 |
| 1000 | 0.000 | 0.001 | 0.000 | 0.000 |
| 1010 | 0.000 | 0.001 | 0.000 | 0.000 |
| 1020 | 0.000 | 0.002 | 0.000 | 0.000 |
| 1030 | 0.000 | 0.002 | 0.000 | 0.000 |
| 1040 | 0.001 | 0.003 | 0.000 | 0.000 |
| 1050 | 0.001 | 0.004 | 0.000 | 0.000 |
| 1060 | 0.002 | 0.007 | 0.000 | 0.000 |
| 1070 | 0.003 | 0.013 | 0.000 | 0.000 |
| 1080 | 0.006 | 0.025 | 0.000 | 0.000 |
| 1090 | 0.011 | 0.043 | 0.001 | 0.000 |
| 1100 | 0.016 | 0.061 | 0.001 | 0.000 |
| 1110 | 0.020 | 0.072 | 0.001 | 0.000 |
| 1120 | 0.023 | 0.079 | 0.001 | 0.000 |
| 1130 | 0.027 | 0.089 | 0.002 | 0.000 |
| 1140 | 0.033 | 0.104 | 0.002 | 0.000 |
| 1150 | 0.041 | 0.125 | 0.003 | 0.000 |
| 1160 | 0.049 | 0.144 | 0.004 | 0.000 |
| 1170 | 0.055 | 0.154 | 0.005 | 0.000 |
| 1180 | 0.056 | 0.154 | 0.005 | 0.000 |
| 1190 | 0.056 | 0.148 | 0.006 | 0.000 |
| 1200 | 0.056 | 0.144 | 0.006 | 0.001 |

Figure 7:
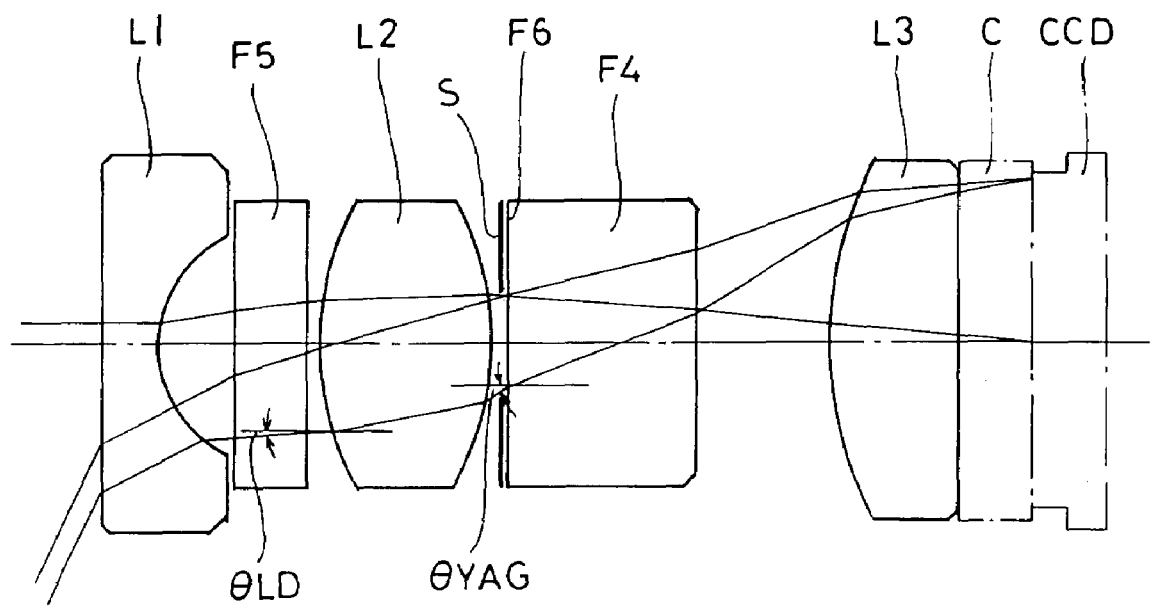
FIG. 7 is a sectional view illustrating a composition of an image pickup system preferred as a third embodiment of the present invention.

A third embodiment is an objective optical system for endoscopes which uses a composite filter such as the first or second embodiment of the present invention as shown in FIG. 7.

This objective optical system for endoscopes comprises, in order from the object side, a negative lens component L1, a positive lens component L2, a stop S, a positive lens component L3 and a cover glass plate C, and uses a reflection type filter F5 disposed between the negative lens component L1 and the positive lens component L2 as well as an absorption type filter F4 disposed between the stop S and the positive lens component L3. That is, the third embodiment uses the composite filter which is described above as the second embodiment.

The objective optical system preferred as the third embodiment is a direct view type optical system which has a field angle of 131° and angle of 0° toward a visual field. Furthermore, a YAG ray cut coating F6 is formed on an object side surface of the absorption type filter (infrared cut filter) F4. Furthermore, the reflection type infrared cut filter F5 has a function to cut off the semiconductor laser rays.

When two or more kinds of reflection type filters are to be used as in the image pickup system preferred as the third embodiment, it is necessary to consider locations of the reflection type filters.

Since a spectral characteristic of a reflection type filter is influenced by an inclination angle of an incident ray, a location of the filter must be considered when the inclination is large.

The reflection type filters F4 and F4 used in the third embodiment are configured so that an angle of incidence θ(LD) of an offaxial ray incident on the absorption type infrared cut filter which also has a function to cut off the semiconductor laser ray and an angle of incidence θ(Y) of the YAG ray cut coating surface F6 satisfy the following condition (2):

$$\theta(LD) < \theta(Y) \quad (2)$$

Since infrared cut filters which have cutoff wavelengths in the vicinity of a visible region largely influence on a color reproducibility, it is desirable to dispose these filters at locations where angles of incidence are larger than that on a TAF ray cut coating. It is therefore desirable to satisfy the above-mentioned condition. Furthermore, it is desirable that these angles of incidence are large to a certain degree since ghost may be produced due to multiple reflections between these coated surfaces. In addition, θ(LD) and θ(Y) are expressed in absolute values in the above-mentioned condition.

Figure 8:
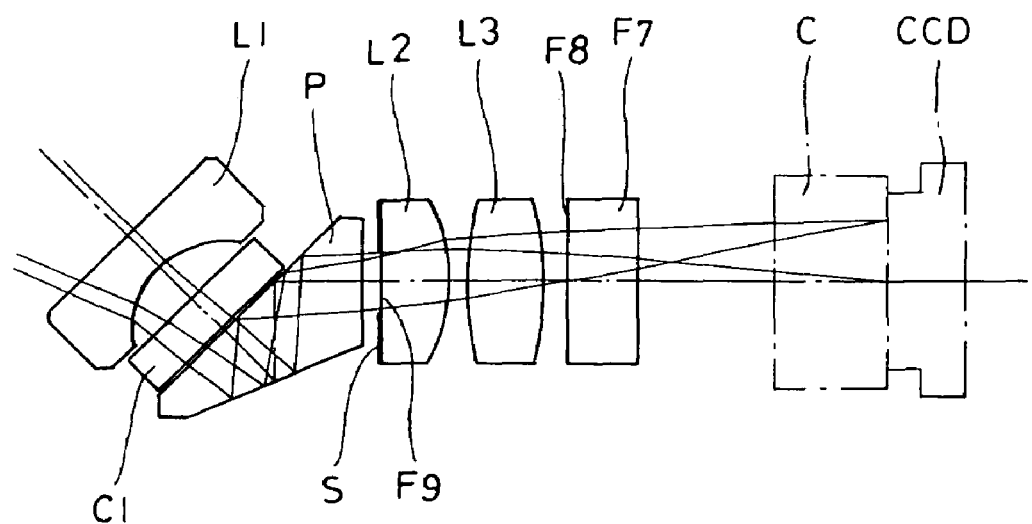
FIG. 8 is a sectional view illustrating a composition of an image pickup system preferred as a fourth embodiment of the present invention.

An objective optical system for endoscopes preferred as a fourth embodiment comprises, in order from the object side as shown in FIG. 8, a negative lens component L1, a cover glass plate C1, a 45° prism P, a stop S, a positive lens component L2, a positive lens component L3, an absorption type infrared cut filter F7, a cover glass plate C and a CCD. The objective optical system preferred as the fourth embodiment is an optical system which has a field angle of 93° and is configured for forward oblique view.

An infrared cut coating which has a function to enhance a color reproducibility and another function to cut off the semiconductor laser ray is formed on an object side surface of the absorption type infrared cut filter F7 used in the optical system preferred as the fourth embodiment. Furthermore, a YAG ray cut coating F9 is formed on an object side surface of the positive lens component L2.

That is, the fourth embodiment uses the composite filter preferred as the first embodiment (the reflection type filter F8 is disposed on the absorption type filter F7) in combination with the YAG our coating formed on the positive lens component L2.

The fourth embodiment also satisfies the above mentioned condition (2).

Furthermore, it is desirable that θ(LD) and θ(Y) satisfy the following condition (3):

$$\theta(LD) < \theta(Y) \leq 25° \quad (3)$$

If the incident angle θ(LD) or θ(Y) is extremely large enough to exceed 25°, color shading will be produces, thereby coloring an image on a monitor. When the condition (3) is satisfied, color shading is not produced and an image is obtained with a high color reproducibility.

Figure 9:
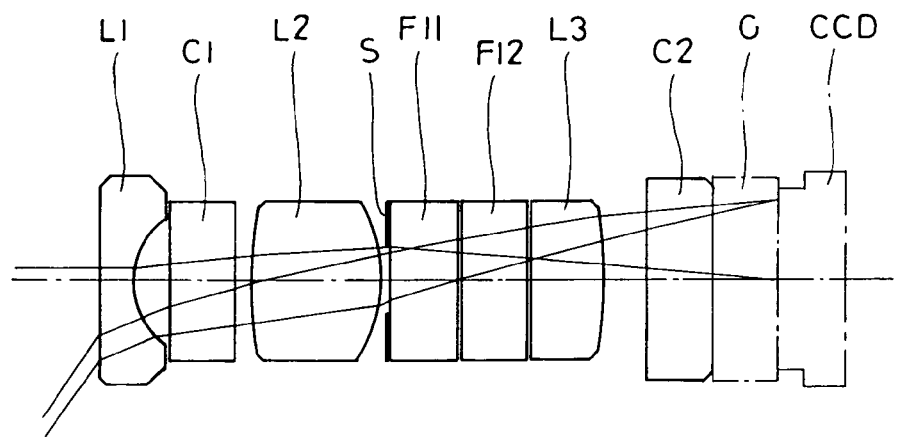
FIG. 9 is a sectional view illustrating a composition of an image pickup system preferred as a fifth embodiment of the present invention.

FIG. 9 shows a fifth embodiment of the present invention which is a direct view type objective optical system for endoscopes which has a field angle of 113°, and comprises, in order from the object side, a negative lens component L1, a cover glass plate C1, a positive lens component L2, a stop S, a reflection type infrared cut filter F11, an absorption type infrared cut filter F12, a positive lens component L3, a cover glass plate C2, a cover glass plate C and a CCD. That is, the fifth embodiment is an objective optical system for endoscopes using the second embodiment which is composed of the reflection type filter F11 and the absorption type filter F12.

The reflection type cut filter used in this optical system has an infrared cut coating having a function to cut off the semiconductor laser which is formed on an object side thereof and a YAG ray cut coating which is formed on a surface thereon on a side of the CCD.

The fifth embodiment is an example wherein a rear lens unit disposed after the stop S is configured to have a composition as simple as possible to facilitate assembly and simplify a structure of a lens barrel, thereby reducing a manufacturing cost.

As seen from FIG. 9, angles of incidence of rays on the filters are sufficiently smaller than those defined by the condition (3). When the angles of incidence are sufficiently small as in the fifth embodiment, influences due to inclination angles of incident rays are small and it is not always necessary to satisfy the condition (2).

Furthermore, angles of incidence of rays on the coatings are nearly equal to each other, and the infrared cut coating having a function to cut off the semiconductor laser ray and the YAG ray cut coating may be formed on either of the surfaces on the reflection type infrared cut filter.

Figure 10:
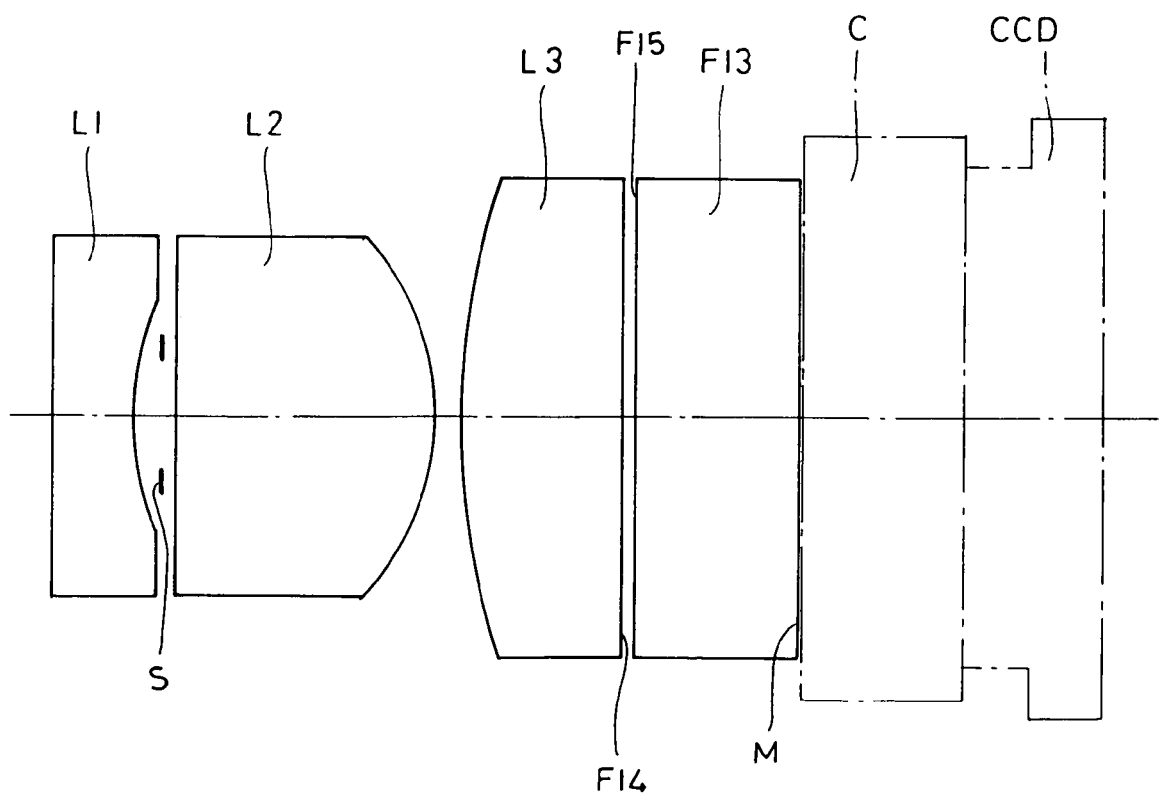
FIG. 10 is a sectional view illustrating a composition of an image pickup system preferred as a sixth embodiment of the present invention.

FIG. 10 shows a sixth embodiment, which comprises, in order from the object side, a negative lens component L1, a stop S, a positive lens component L2, a positive lens component L3, an absorption type cut filter F13, a cover glass plate C and a CCD: an infrared cut coating F14 having a function to cut off the semiconductor laser ray being formed on a surface of the positive lens component L3 which is on a side of the CCD and a YAG ray cut coating F15 being formed on an object side surface of the absorption type infrared cut filter F13. That is, the sixth embodiment is an example wherein the YAG cut coating F15 is additionally formed on the composite filter preferred as the second embodiment which consists of the absorption type filter F13 and the reflection type filter F14.

Like the fifth embodiment, the sixth embodiment is an example wherein the angles θ(LD) and θ(Y) are made sufficiently small. As compared with the fifth embodiment, the sixth embodiment is characterized in that it has a simpler composition and is configured more compact. Speaking more concretely, the stop S is disposed at a location shifted toward the object side, and stronger powers are imparted to the positive lens components L2 and L3 to configure the sixth embodiment to be more compact and thinner.

In the sixth embodiment, a mask M which restricts a visual field and prevent detrimental rays is formed by depositing chromium on a surface of the absorption type infrared filter F13 on the side of the CCD. Owing to the configuration described above, the sixth embodiment has the simpler composition as described and can be assembled more easily.

The sixth embodiment is a direct view type objective optical system for endoscopes having a field angle of 114°.

Figure 11:
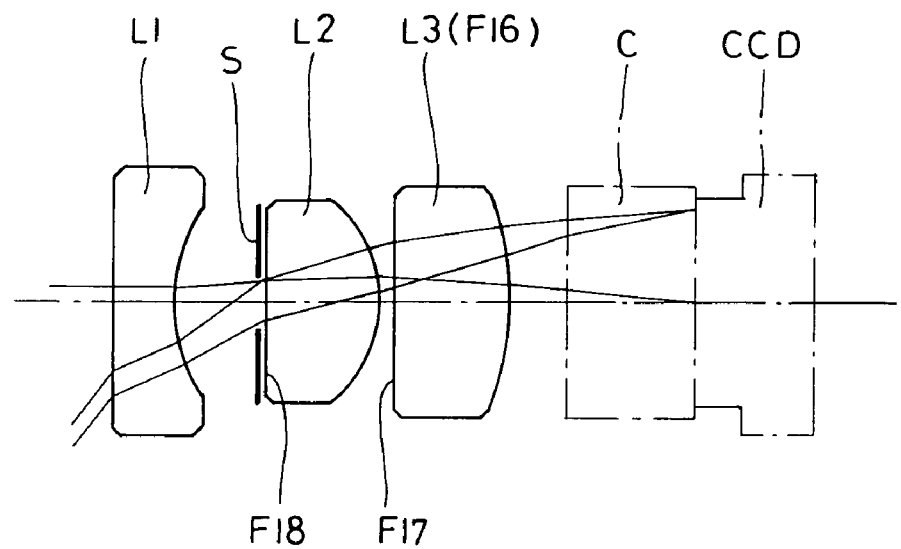
FIG. 11 is a sectional view illustrating a composition of an image pickup system preferred as a seventh embodiment of the present invention.

FIG. 11 is a sectional view illustrating an optical system preferred as a seventh embodiment, which comprises, in order from the object side, a negative lens component L1, a stop S, a positive lens component L2, a lens (infrared cut lens) component L3, a CCD cover glass plate C and a CCD.

The seventh embodiment uses the positive lens component L3 having an infrared cut function as a filter F16. In other words, curvature is imparted to an absorption type infrared cut filter so that it functions as a positive lens component. This infrared cut filter makes it possible to save a space to dispose a filter, thereby making the optical system and a tip of an endoscope more compact. Furthermore, a YAG laser cut coating is formed on an object side surface of the positive lens component L2 and a reflection type infrared cut coating F17 is formed on an object side surface of the infrared cut lens F16 (positive lens component L3). Furthermore, it is possible to configure this reflection type infrared cut coating F16 so as to have a semiconductor laser ray cut function.

The absorption type infrared cut filter F16 may be manufactured by a sol-gel method. This method enhances water resistance, abrasion resistance and a workability of the filter. When an absorption type infrared cut filter is worked so as to have a spherical surface as in the seventh embodiment, the sol-gel method effectively enhances a workability of the filter.

Figure 12:
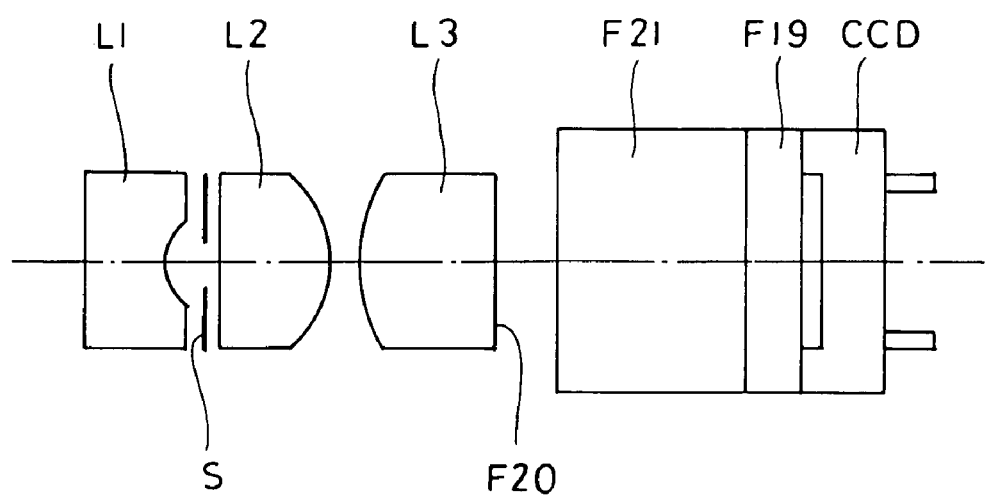
FIG. 12 is a sectional view illustrating a composition of an image pickup system preferred as an eighth embodiment of the present invention.

FIG. 12 is a sectional view illustrating an eighth embodiment of the present invention, which comprises, in order from the object side, a negative lens component L1, a stop S, a positive lens component L2, a positive lens component L3, an absorption type YAG ray cut filter F21, an absorption type infrared cut filter F19 and a CCD. Furthermore, a reflection type infrared cut coating F20 is formed on a surface of the positive lens component L3 which is located on a side of the CCD. That is, an optical system preferred as the eighth embodiment uses a composite filter which consists, like the filter in the second embodiment, of the absorption type infrared cut filter F19, the reflection type infrared cut filter F20 disposed on the positive lens component L3 and the absorption type cut filter F21. The composite cut filter used in the eighth embodiment consists of a first optical element F19 which is the absorption type cut filter, a second optical element F20 which is the reflection type cut filter and a third optical element F21 which is the absorption type cut filter.

The eighth embodiment is an example wherein ghost and flare are reduced by disposing the absorption type infrared cut filter F19 and the YAG ray cut filter F21. The reflection type infrared cut coating is formed on the surface of the positive lens component L3 which is located on the side of the CCD.

Ghost and flare can be reduced sufficiently by using a YAG ray cut coating which is a surface having high reflectance as an absorption type filter as described above. In the eighth embodiment, Infrared Cut Filter HA-15 prepared by HOYA is used as the absorption type YAG ray cut filter F21 which can cut off infrared rays having a wavelength region from 1000 nm to 1200 nm. 11A-30 prepared by HOYA having a smaller absorption coefficient for infrared rays may be used with an endoscope which has a margin in a size (length) of its tip.

In other words, it is desirable to select an absorption type infrared cut filter having an adequate absorption coefficient dependently on a size of a tip of an endoscope.

Figure 13:
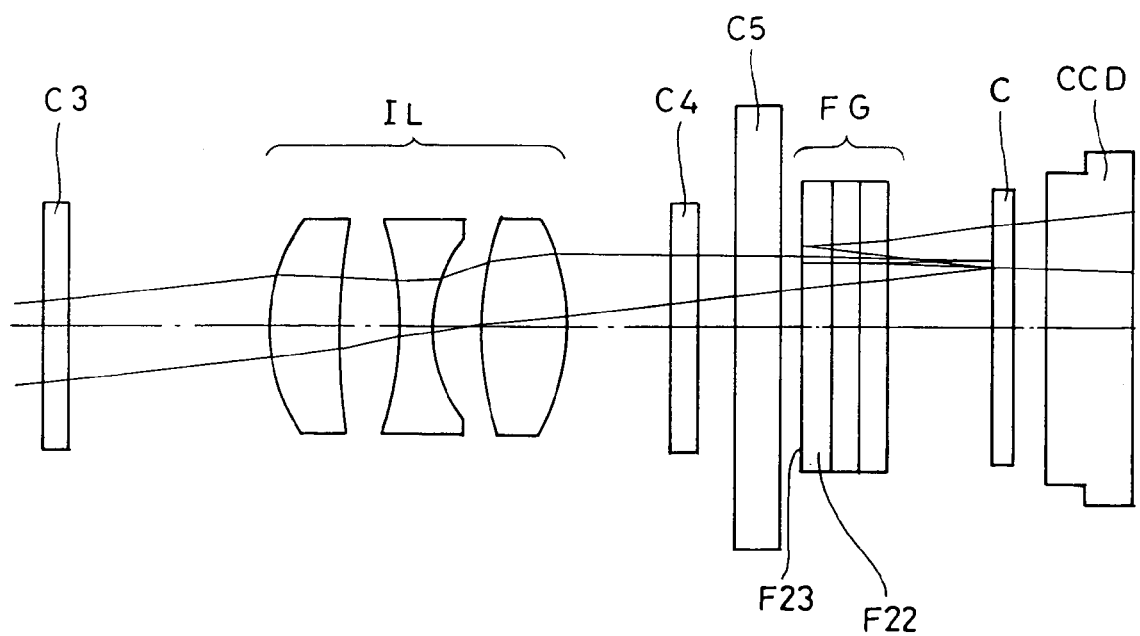
FIG. 13 is sectional view illustrating a composition of an image pickup system preferred as a ninth embodiment of the present invention.

FIG. 13 illustrates a ninth embodiment. The ninth embodiment is an example wherein a reflection type infrared out filter is used in a TV adaptor for endoscopes. The ninth embodiment comprises, in order from the object side as shown in FIG. 13, a cover glass plate C3, an imaging lens system IL which consists of a positive lens component, a negative lens component and a positive lens component, a cover glass plate C4, a cover glass plate C5, a filter group FG, a CCD cover glass plate C and a CCD. A filter F22 which is disposed on the object side in the filter group FG and has an infrared cut coating F23 formed thereon functions so that a light bundle which is incident from the object side and has passed through the infrared cut coating F23 is reflected by a surface having high reflectance such as the CCD cover glass plate C and then is reflected once again by the infrared cut coating, thereafter being incident on an image pickup surface of the CCD a ghost.

Figure 14:
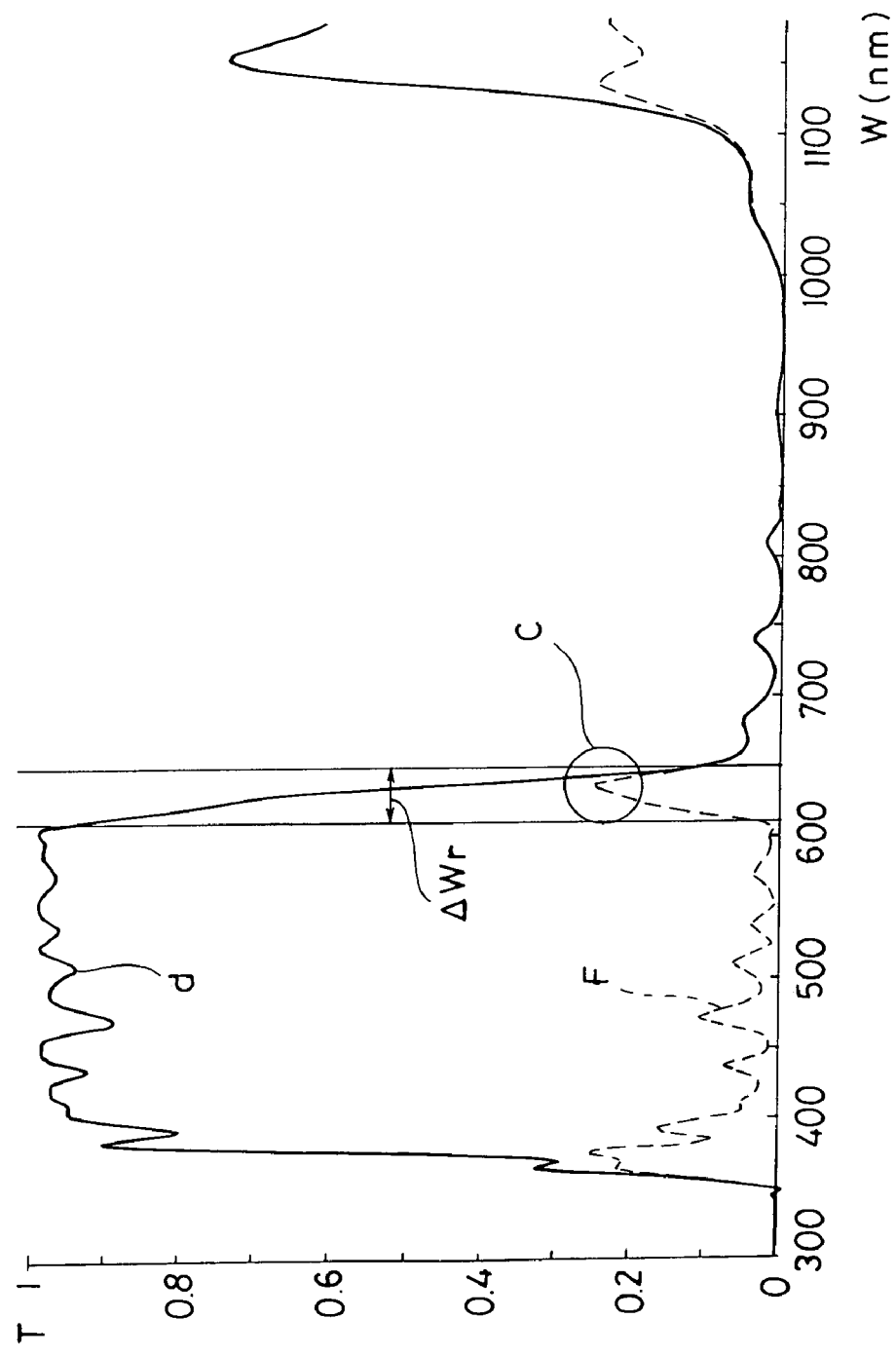
FIG. 14 is a diagram illustrating a spectral characteristic of ghost rays in the ninth embodiment of the present invention.

FIG. 14 shows a spectral curve of a reflection type infrared cut filter. When transmittance of a coating surface is represented by τ, reflectance of the coating surface is designated by (1−τ), transmittance for ghost rays is approximately expressed as r×(1−τ), whereby an intensity distribution is as indicated in a portion C of FIG. 14. The ghost rays can be reduced by narrowing an area of the portion C of FIG. 14. In other words, it is sufficient for reducing ghost rays to make an inclination of the spectral curve steeper in a cutoff region $\Delta W_\tau$.

It is desirable that at least a reflection type infrared cut filter of a composite filter to be used in the ninth embodiment has a cutoff frequency region $\Delta W_\tau$ of 610 nm to 650 nm at which it exhibits transmittance not higher than 10% as well as transmittance not lower than 50% at a wavelength of 610 nm and transmittance not higher than 10% at a wavelength of 650 nm.

The condition described above is defined taking into consideration manufacturing errors of the filters and shifts of spectral characteristics dependent on angles of incidence on a coating.

The cutoff wavelength region is apt to be generally narrowed by making the inclination of the spectral curve steeper and it is effective for reducing ghost and noise to combine the reflection type infrared cut filter with an absorption type infrared cut filter, thereby composing a composite filter.

When the condition described above is not satisfied, ghost rays are noticeable and a steep cutoff characteristic cannot be obtained, thereby making it impossible to except enhancement of a color reproducibility.

Figure 15A:
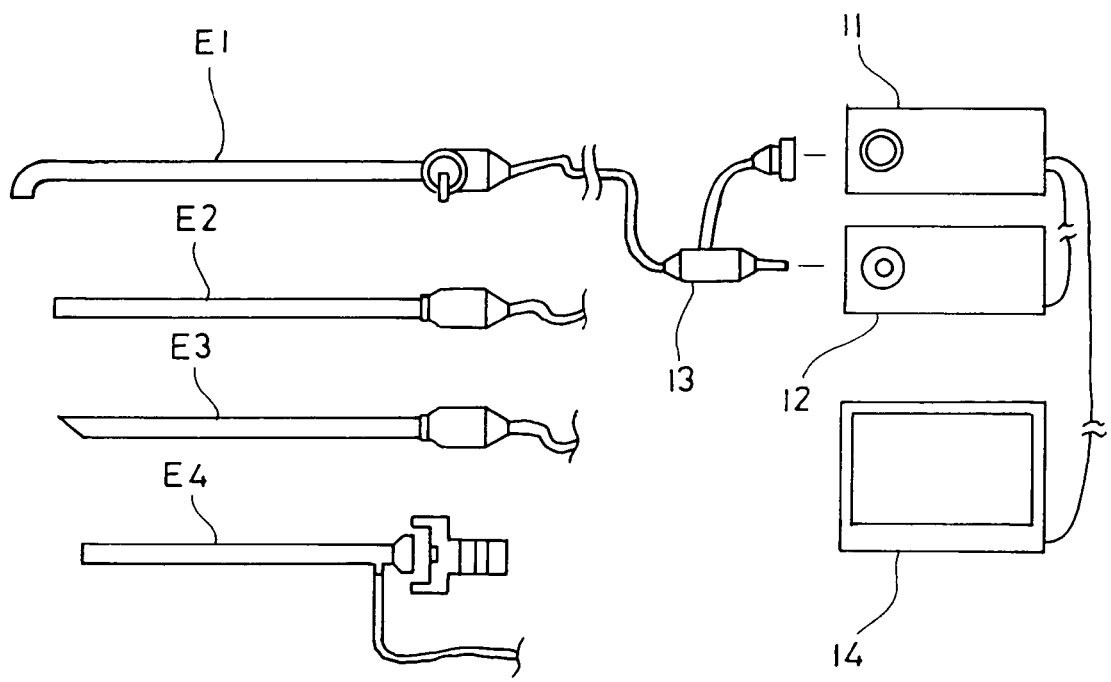
FIG. 15A is a diagram illustrating a configuration of an endoscope system preferred as a tenth embodiment of the present invention.

FIG. 15A shows an endoscope system consisting of endoscopes which adopt the composite filter preferred as the first embodiment of the present invention. This system controls a plurality of endoscopes with a single CCU (camera control unit) as shown in FIG. 15A. In FIG. 15A, a reference numeral 10 represents an endoscopes set which consists of a plurality of endoscopes E1, E2, . . . a reference numeral 11 designates the CCU, a reference numeral 12 denotes a light source, a reference numeral 13 represents a signal cable including a light guide cable and a reference numeral 14 designates a TV monitor.

The endoscope system is equipped with the plurality of endoscopes E1, E2, . . . which have specifications optimum for needs in fields of products of optical instruments. The absorption type infrared cut filters which are relatively inexpensive are mainly used, for example, in a medical endoscope for digestive systems and an external TV camera whose sizes are little restricted. In case of an endoscope for bronchi whose size is restricted relatively severely, the reflection type filters are used to meet a demand for a compact design. Furthermore, CCDs optimum for respective fields of products of optical instruments are used. It is therefore required to compose an endoscope such as that shown in FIG. 15A.

It is presumed that the plurality of endoscopes to be used in such an endoscope system use different kinds of filters and different kinds of CCDs, whereby the endoscopes have different color reproducibilities and can hardly be controlled with a single CCU.

In an endoscope system such as that described above, it is effective to use the composite filter according to the present invention for each of a plurality of endoscopes. It is desirable, for example, to optimize a spectral characteristic of the composite filter to each endoscope so as to nearly equalize color reproducibilities of endoscope images which are to be finally obtained.

The composite filter according to the present invention permits modifying its spectral characteristic since it is composed of the reflection type and the absorption type filters which have different spectral characteristics. For such a modification of the spectral characteristic of the composite filter it is possible to change a thickness of the absorption type filter and only a film configuration of the reflection type filter.

When color reproducibilities cannot be equalized with the composite filter according to the present invention or when it is not desired to use a plurality of different filters, a plurality of color matrix circuits may be prepared on the side of the CCU so that an endoscope system can selects a color matrix circuit optimum for each product. For example, an endoscope system may be configured to select an electric resistor in a CCD connector for each endoscope and select a color matrix by detecting a signal from the electric resistor on the side of the CCU. Alternately, the endoscope system may be configured to be capable of selecting color matrices which are customized by a user for ways of use.

Not only electronic endoscopes but also non-flexible endoscopes connected to an external TV set and fiber scopes are usable in the endoscope system according to the present invention.

In order to perform "white balance" process in a CCU used in such an endoscope system, it is general to process the color signals R, G and B by multiplying them by certain coefficients so that they are "white" set on the side of the CCU. In such a case, it is possible to obtain a color reproducibility with higher fidelity by using a color compensation circuit which performs color correction, for example, also of red simultaneously with that of white. It is possible to use a circuit which is capable of color correction of the three primary colors of red, green and blue respectively.

Figure 15B:
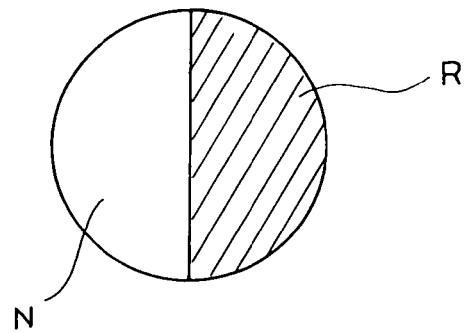
FIG. 15B is a diagram showing a white-red mixture color chart to be used in the endoscope system shown in FIG. 15A.

Though a white chart or the like is usually used for manual color correction, a white-red mixture color chart (for example R is red and W is white) such as that shown in FIG. 15B may be used.

The image pickup apparatus according to the present invention which uses the composite filter having the total spectral characteristic is capable of enhancing a color reproducibility, produces little ghost and flare, and reducing electric noise.

The endoscope system according to the present invention is capable of obtaining which is nearly constant even when it uses any one of a plurality of different kinds of endoscopes.

What is claimed is:

1. An image pickup apparatus comprising:
   an image pickup device which comprises an optical element absorbing rays having specific wavelengths, a second optical element reflecting rays having specific wavelengths and an image pickup device having an organic color mosaic filter,
   wherein a total spectral characteristic of a combination of said optical element absorbing the rays having the specific wavelengths and said optical element reflecting the rays having the specific wavelengths satisfies the following condition (1):

$$0.45 \leq |\Delta T/\Delta W| \leq 0.75 \tag{1}$$

wherein the reference symbol $\Delta T$ is given by an equation shown below when transmittance at a wavelength of 550 nm is represented by T(550) and transmittance at a wavelength of 600 nm is designated by T(600), $\Delta T = T(600) - T(550)$, and the reference symbol $\Delta W$ denotes 50 nm.

2. The image pickup system according to claim 1 comprising another optical element which has a spectral characteristic different from that of said second optical element and reflects rays having specific wavelengths, wherein said another optical element has transmittance not higher than 10% at wavelengths of 1060±20 nm.

3. The image pickup apparatus according to claim 2 satisfying the following condition (2):

$$\theta(LD) < \theta(Y) \qquad (2)$$

wherein the reference symbol $\theta(LD)$ represents an inclination angle of a ray incident on said another optical element which reflects the rays having the specific wavelengths and the reference symbol $\theta(Y)$ designates an inclination angle of a ray incident on said another optical element which reflects the rays having the specific wavelengths.

4. The image pickup apparatus according to claim 3, further satisfying the following condition (3):

$$\theta(LD) < \theta(Y) \leq 25° \qquad (3).$$

5. The image pickup apparatus according to claim 2, 3 or 4 comprising an optical element disposed in place of said optical element which reflects the rays having the specific wavelengths, wherein said optical element absorbs rays having specific wavelengths and has a spectral characteristic different from that of said optical element which absorbs the rays having the specific wavelengths.

6. The image pickup apparatus according to claim 5, wherein said another optical element which absorbs the rays having the specific wavelengths is configured as a sealing member for the image pickup device.

7. The image pickup apparatus according to claim 1, wherein a cutoff wavelength at which at least one of the optical elements reflecting the rays having the specific wavelengths has transmittance not higher than 10% exists within a wavelength region from 610 to 650 nm, and said image pickup apparatus has transmittance not lower than 50% at a wavelength of 610 nm and transmittance not higher than 10% at a wavelength of 650 mm.

8. The image pickup apparatus according to claim 1, wherein the optical element which absorbs the rays having the specific wavelength is manufactured by a sol-gel method.

9. An endoscope system comprising:
a set of a plurality of endoscopes;
a camera control unit;
a light source unit; and
a monitor,
wherein each endoscope of said plurality of endoscopes comprises:
an objective lens system;
a filter; and
an image pickup device;
wherein at least one of said plurality of endoscopes is equipped with the objective lens system, the filter and the image pickup device, at a tip of an insert section,
wherein said plurality of endoscopes are selectively connected to said camera control unit,
wherein an object is irradiated with rays emitted from said light source unit,
wherein said monitor displays an image formed by an endoscope which is connected to said camera control unit,
wherein a spectral characteristic of the image pickup device of one of said endoscopes is different from spectral characteristics of the image pickup device of the other endoscopes,
wherein the filter of each endoscope is at least one of an optical element which absorbs rays and an optical element which reflects rays, and
wherein a total spectral characteristic of said image pickup device and said optical element is predetermined for each of said endoscopes.

10. The endoscope system according to claim 9, wherein said filters used in said plurality of endoscopes have thicknesses which are different dependently on said endoscopes.

11. The endoscope system according to claim 9, wherein said camera control unit comprises a plurality of color matrices, and has a function to select one of the color matrices for each endoscope to which a color matrix circuit of the control unit so that color reproducibilities are nearly constant on said TV monitor when said plurality of endoscopes are connected to said camera control unit.

12. An endoscope system comprising:
a set of a plurality of endoscopes;
a camera control unit;
a light source unit; and
a monitor,
wherein each endoscope of said plurality of endoscopes comprises:
an objective lens system;
a filter; and
an image pickup device;
wherein at least one of said plurality of endoscopes is equipped with the objective lens system, the filter and the image pickup device, at a tip of an insert section,
wherein said plurality of endoscopes are selectively connected to said camera control unit,
wherein an object is irradiated with rays emitted from said light source unit,
wherein said monitor displays an image formed by an endoscope which is connected to said camera control unit,
wherein a spectral characteristic of the image pickup device of one of said endoscopes is different from spectral characteristics of the image pickup device of the other endoscopes,
wherein the filter of each endoscope is at least one of an optical element which absorbs rays and an optical element which reflects rays, and
wherein a total spectral characteristic of said image pickup device and said optical element is predetermined for each of said endoscopes,
wherein the total spectral characteristic of said optical elements of each endoscope satisfies the following condition (1)

$$0.45 \leq |\Delta T/\Delta W| \leq 0.75, \qquad (1)$$

wherein the reference symbol $\Delta T$ is given by an equation shown below when transmittance at a wavelength of 550 nm is represented by T(550) and transmittance at a wavelength of 600 nm is designated by T(600), $\Delta T = T(600) - T(550)$, and the reference symbol $\Delta W$ denotes 50 nm.

13. A composite filter comprising an optical element which absorbs rays having specific wavelengths; and an optical element which reflects rays having specific wavelengths, wherein a total spectral characteristic of a combination of said optical elements which absorbs the rays having the specific wavelengths and said optical element which reflects the rays having the specific wavelengths has transmittance not lower than 40% at a wavelength of 600 nm, transmittance of 5% at a wavelength of 700 nm and $A=|\Delta T/\Delta W|=0.6\pm0.1$, wherein the reference symbol $\Delta T$ represents a difference between the transmittance T(600) at the wavelength of 600 nm and the transmittance T(550) at the wavelength of 550 nm, and the reference symbol $\Delta W$ designates 50 nm.

14. An image pickup apparatus comprising:

an image pickup device which comprises an optical element absorbing rays having specific wavelengths, a second optical element reflecting rays having specific wavelengths and an image pickup device having an organic color mosaic filter, wherein a total spectral characteristic of a combination of said optical element absorbing the rays having the specific wavelengths and said optical element reflecting the rays having the specific wavelengths satisfies the following condition (1—1):

$$0.35 \leq A \leq 0.75 \qquad (1—1)$$

wherein $A=|\Delta T/\Delta W|$ and the reference symbol $\Delta T$ is given by an equation shown below when transmittance at a wavelength of 550 nm is represented by T(550) and transmittance at a wavelength of 600 nm is designated by T(600), $\Delta T=T(600)-T(550)$, and the reference symbol $\Delta W$ denotes 50 nm.

\* \* \* \* \*